United States Patent [19]

Hunag

[11] Patent Number: 5,391,736
[45] Date of Patent: Feb. 21, 1995

[54] PREPARATION OF 2,4,6-TRINITRO-2,4,6-TRIAZA-CYCLOHEXANONE

[75] Inventor: Der-Shing Hunag, Folsom, Calif.

[73] Assignee: Gencorp Aerojet, Rancho Cordova, Calif.

[21] Appl. No.: 471,906

[22] Filed: Jan. 29, 1990

[51] Int. Cl.$^6$ ............................................ C07D 251/08
[52] U.S. Cl. .............................................. 544/220
[58] Field of Search ........................................ 544/220

[56] References Cited

U.S. PATENT DOCUMENTS

| | | | |
|---|---|---|---|
| 2,016,521 | 10/1935 | Steindorff et al. | 260/27 |
| 3,696,101 | 10/1972 | Litt et al. | 260/248 NS |
| 3,899,489 | 8/1975 | Horlein et al. | 260/248 NS |
| 4,084,054 | 4/1978 | Frump | 544/220 |

*Primary Examiner*—Philip Tucker
*Attorney, Agent, or Firm*—Townsend and Townsend, Khourie and Crew

[57] ABSTRACT

A method for the preparation of 2,4,6-trinitro-2,4,6-triaza-cyclohexanone yielding a product with a low concentration of impurities which results in improved thermal stability is disclosed, the method involving the use of either 2-nitroimino-5-nitrohexahydro-1,3,5-triazine or an acid salt of 2-nitroimino-hexahydro-1,3,5-triazine as starting materials, with a mixture of reagents comprising $(CF_3CO)_2O$ and either $HNO_3$ or $NH_4NO_3$. The product is advantageous compared with RDX and HMX since it is more energetic and has a higher density.

28 Claims, No Drawings

PREPARATION OF 2,4,6-TRINITRO-2,4,6-TRIAZA-CYCLOHEXANONE

BACKGROUND OF THE INVENTION

This invention is in the field of energetic munitions compounds, and particularly cyclic nitramines.

The propellant industry is constantly striving for compounds that have high energy and high density characteristics for use in munitions, including both explosives and propellants. Some current high volume ingredients such as cyclotrimethylenetrinitramine (RDX) and cyclotetramethylenetetranitramine (HMX) are very effective in providing energy for numerous munitions applications. The industry, however, continues to seek new compounds having densities near 2.0 g/mL, detonation pressures greater than 400 kbar, detonation velocities greater than 9000 m/sec, favorable oxygen balance, and good thermal and hydrolytic stability.

One candidate for this type of energetic compound is 2,4,6-trinitro-2,4,6-triaza-cyclohexanone (TNTC). This compound has a calculated density of near 2.0 g/mL, a favorable oxygen balance, a calculated detonation velocity of 9270 m/sec, and a calculated detonation pressure of 402 kbar. A comparison of the thermochemical properties of TNTC with those of RDX and HMX is shown in the table below.

TABLE I

Thermochemical Properties of RDX, HMX and TNTC
(All values listed below are calculated values, except those marked with an asterisk, which are observed.)

|  | RDX | HMX | TNTC |
|---|---|---|---|
| Empirical Formula | $C_3H_6N_6O_6$ | $C_4H_8N_8O_8$ | $C_3H_4N_6O_7$ |
| Oxygen Balance, % | −21.6 | −21.6 | −6.8 |
| Heat of Formation, kcal/mole | +14.7* | +17.9* | −14.8 |
| Heat of Explosion, kcal/100 g | −120 | −120 | −134 |
| Detonation Velocity, m/sec | 8850 | 9160 | 9270 |
| Detonation Pressure, kbar | 350 | 382 | 402 |
| Density, g/mL | 1.82* | 1.90* | 1.97 |

These figures show that TNTC is more energetic and more dense than both RDX and HMX. TNTC has a lower heat of formation but a more favorable oxygen balance than either of the other two. In addition, differential scanning calorimetry measurements show that TNTC has a sharp exotherm peak at 206° C.

Known methods for forming TNTC involve reacting urea with formaldehyde and t-butylamine to give 4-t-butyltetrahydro-1,3,5-triazin-2-one, followed by nitration and nitrolysis to achieve the desired product. This procedure suffers from a low overall reaction yield and a product having less than optimal thermal stability, the latter possibly attributable to the presence of a high proportion of impurities.

SUMMARY OF THE INVENTION

A method for preparing 2,4,6-trinitro-2,4,6-triazacyclohexanone has now been developed, which uses either 2-nitroimino-5-nitrohexahydro-1,3,5-triazine, or 2-nitroimino-hexahydro-1,3,5-triazine acid salt, as a starting material. The starting material is reacted with a reagent mixture comprising $(CF_3CO)_2O$ (trifluoroacetic anhydride) and either $HNO_3$ or $NH_4NO_3$ (ammonium nitrate). Preferred starting materials are 2-nitroimino-5-nitrohexahydro1,3,5-triazine and 2-nitroimino-hexahydro-1,3,5-triazine hydrochloride, and the preferred nitrating agent mixture is $(CF_3CO)_2O$ and $NH_4NO_3$. The reaction is generally run in a solvent, the preferred solvent being nitromethane ($CH_3NO_2$).

Operating conditions and the various parameters of the method, as well as further features and advantages of the invention are set forth below.

DETAILED DESCRIPTION OF THE INVENTION AND PREFERRED EMBODIMENTS

The compound 2,4,6-trinitro-2,4,6-triazacyclohexanone (TNTC) is represented by the formula

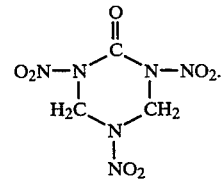

The compound 2-nitroimino-5-nitrohexahydro-1,3,5-triazine (NNHT) is represented by the formula

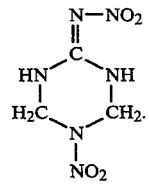

The compound 2-nitroimino-hexahydro-1,3,5-triazine (NIHT) is represented by the formula

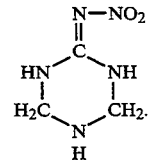

The compound 2-nitroimino-hexahydro-1,3,5-triazine is used in the form of an acid salt, of which examples are salts formed from hydrohalic acids, sulfuric acid, phosphoric acid, acetic acid and nitric acid. Hydrohalide salts are preferred, more preferably those in which the halogen is chlorine, bromine or iodine, and most preferably the hydrochloride salt. NNHT may be prepared from NIHT as described below.

The amounts of the reagents in the reagent mixture relative to each other are likewise not critical and may vary widely. In preferred embodiments, the mole ratio of any two components in the mixture (referring to the nitrating agents only) will range from about 1.0 to about 3.0, most preferably from about 1.0 to about 1.5.

The reaction may be conducted in any nonreactive atmosphere, including atmospheric air as well as atmospheres of inert gas, such as nitrogen for example. As for the temperature, it is preferred that the initial stages of the reaction be conducted at temperatures below 10° C., most preferably from about 0° C. to about 5° C. The reaction mixture can then be permitted to warm to ambient temperature to complete the reaction.

The reaction is generally conducted in the presence of a solvent. Examples of suitable solvents are nitromethane, chloroform and acetonitrile, although other solvents may be used as well. Nitromethane is the preferred solvent. The solvent may be used in any proportion.

For those procedures starting with the nitration of an NIHT acid salt, notably the hydrochloride salt, to form NNHT, the nitration is effected by a conventional nitrating agent. Examples are nitric acid and a mixture of nitric and sulfuric acids at proportions and according to procedures well known among those skilled in the art. This reaction is preferably done at a temperature of less than about 5° C., preferably from about −20° C. to about 5° C., and most preferably from about −20° C. to about −10° C. NIHT itself may be prepared from hexamethylenetetramine and nitroguanidine in an acidic reaction medium, such as for example aqueous HCl, in which case the product will be the hydrochloride salt. The preferred conditions for this reaction is a temperature of from about 20° C. to about 50° C.

Following completion of the reaction to form TNTC, the product TNTC is recovered from the reaction mixture and purified by conventional techniques, including evaporation in vacuo, filtration, and other common methods. The product may be purified by recrystallization from a variety of organic solvents, preferably ethyl acetate.

The following examples are offered solely for purposes of illustration, and are intended neither to limit nor to define the invention in any manner.

EXAMPLE 1

PREPARATION OF 2,4,6-TRINITRO-2,4,6-TRIAZA-CYCLOHEXANONE FROM 2-NITROIMINO-5-NITROHEXAHYDRO-1,3,5-TRIAZINE

A three-neck 100 mL flask fitted with a condenser, a magnetic stirrer, and a thermometer, and provided with a positive nitrogen atmosphere was charged with trifluoroacetic anhydride ($(CF_3CO)_2O$) (12 mL, 84.96 mmoles) and nitromethane (40 mL, 74.2 mmoles). The mixture was chilled to 3.8° C. in an ice bath, and ammonium nitrate (4.85 g, 60.59 mmoles) was added in one portion. The mixture was stirred for forty minutes, with trace amounts of ammonium nitrate remaining undissolved. To the mixture was then added 2-nitroimino-5-nitrohexahydro1,3,5-triazine (NNHT) (3.82 g, 20.09 mmoles) in several portions at 3.8° C. to 5.2° C. over a fifteen-minute period. Upon the completion of the NNHT addition, the reaction mixture first became a clear light yellow solution, then gradually turned cloudy and became a white slurry mixture within twenty minutes. The slurry mixture was held at 2.8°–4.5° C. for 6.5 hours, then gradually warmed to ambient temperature (19° C.) overnight. The mixture, still a white slurry, was then stripped in vacuo at a temperature of 20°–25° C. to near dryness, quenched with 75 mL of deionized water at ambient temperature (20° C.), filtered, washed with 20 mL of deionized water, and dried in vacuo (20°–40° C., 0.5 mm Hg) to give a white solid weighing 2.95 g (62.2% yield).

The structure was confirmed as that of 2,4,6-trinitro-2,4,6-triaza-cyclohexanone (TNTC) by proton NMR and FTIR as follows:

proton NMR ($d^6$-DMSO): δ6.1 (s, —($O_2N$)N$CH_2$N-($NO_2$)—)

FTIR (KBr): 3056 cm$^{-1}$ (CH stretch), 1765 cm$^{-1}$ (—C=O stretch), 1606 cm$^{-1}$ (—$NNO_2$ asymmetric stretch), 1282 cm$^{-1}$ (—$NNO_2$ symmetric stretch)

An impact test (Bureau of Mines) indicated shock sensitivity at a height of 9 cm for a 2 kg weight.

The white solid was recrystallized from ethyl acetate to give off-white crystals, with m.p. 195° C. (with decomposition), CIMS (isobutane) m/z 237 (MH+). An exotherm onset was determined by differential scanning calorimetry (DSC) as 183.9° C., with an exotherm peak at 206.3° C. Elemental analysis was as follows: calculated for $C_3H_4N_6O_7$: C, 15.26; H, 1.71; N, 35.60; found: C, 15.71; H, 1.73; N, 35.44.

EXAMPLE 2

PREPARATION OF 2,4,6-TRINITRO-2,4,6-TRIAZA-CYCLOHEXANONE FROM 2-NITROIMINO-5-NITROHEXAHYDRO-1,3,5-TRIAZINE

The procedures of Example 1 were repeated, using however 12 mL (84.96 mmoles) of trifluoroacetic anhydride, 40 mL (74.12 mmoles) of nitromethane, 4.8 g (60.0 mmoles) of ammonium nitrate, and 1.90 g (10.0 mmoles) of NNHT. The product was a white solid weighing 1.77 g (75.0% yield) after workup, with proton NMR and FTIR spectra identical to that of the product of Example 1.

EXAMPLE 3

PREPARATION OF 2,4,6-TRINITRO-2,4,6-TRIAZA-CYCLOHEXANONE FROM 2-NITROIMINO-HEXAHYDRO-1,3,5-TRIAZINE HYDROCHLORIDE

The procedures of Example 1 were repeated, using however a 50 mL three-neck flask, and the following reactants: 2-nitroimino-hexahydro-1,3,5-triazine hydrochloride (NIHT.HCl) (0.91 g, 5.02 mmoles), 2.46 g of ammonium nitrate (30.75 mmoles), 6 mL of trifluoroacetic anhydride (42.48 mmoles) and 20 mL of nitromethane (37.06 mmoles). Upon workup, the product TNTC weighed 0.5 g, and was obtained together with an unidentified by-product at approximately a 1:1 weight ratio.

EXAMPLES 4–10

The procedures of Example 1 were applied to a series of runs, using NNHT as the starting material, varying in the proportions and components of the reagent mixture and the solvent used. Results are given in Table II below.

TABLE II

| | | | | | TNTC Product | |
|---|---|---|---|---|---|---|
| NNHT (g) | $NH_4NO_3$ (g) | $HNO_3$* (mL) | $(CF_3CO)_2O$ (mL) | Solvent | weight (g) | yield (%) |
| 1.90 | 4.80 | — | 12 | $CH_3NO_2$, 40 mL | 1.77 | 75.0 |
| 3.82 | 4.85 | — | 12 | $CH_3NO_2$, 40 mL | 2.95 | 62.2 |

Experimental Results - Examples 4–10

TABLE II-continued

| Experimental Results - Examples 4–10 | | | | | TNTC Product | |
|---|---|---|---|---|---|---|
| NNHT (g) | NH$_4$NO$_3$ (g) | HNO$_3$* (mL) | (CF$_3$CO)$_2$O (mL) | Solvent | weight (g) | yield (%) |
| 3.82 | 4.85 | — | 12 | CH$_3$COOH, 40 mL | 0 | 0 |
| 1.91 | 2.48 | — | 6 | CHCl$_3$, 40 mL | 0.58 | 24.5 |
| 3.82 | 4.85 | — | 12 | CHCl$_3$, 40 mL | 0.42 | 8.9 |
| 3.83 | 4.86 | — | 12 | CH$_3$CN, 40 mL | 0.76 | 16.0 |
| 1.02 | — | 3.00 | 20 | — | 0.72 | 56.8 |

*99% HNO$_3$

EXAMPLE 11—COMPARISON EXAMPLE

This example involves the use of a reagent outside the scope of the present invention and is included for purposes of comparison. In this example, the procedure of Example 1 was again followed, using acetic anhydride in place of trifluoroacetic anhydride, and the result was that no reaction occurred. Table III lists the proportions and components of the reaction mixture in the same format as Table II.

TABLE III

| Experimental Results - Example 11 | | | | TNTC Product | |
|---|---|---|---|---|---|
| NNHT (g) | NH$_4$NO$_3$ (g) | (CH$_3$CO)$_2$O (mL) | Solvent | weight (g) | yield (%) |
| 1.91 | 2.40 | 6 | CH$_3$NO$_2$, 20 mL | 0 | 0 |

The foregoing is offered primarily for purposes of illustration. It will be readily apparent to those skilled in the art that numerous variations, modifications and substitutions in terms of the materials, procedures and conditions disclosed above may be made without departing from the spirit and scope of the invention.

What is claimed is:

1. A method for the preparation of a compound having the formula

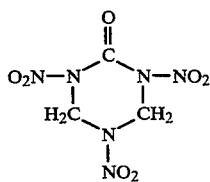

comprising reacting a starting material having the formula

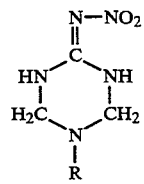

in which R is a member selected from the group consisting of H.(acid salt) and NO$_2$, with a reagent mixture comprising a combination of (a) (CF$_3$CO)$_2$O and (b) a member selected from the group consisting of HNO$_3$ and NH$_4$NO$_3$.

2. A method in accordance with claim 1 in which each reagent in said reagent mixture is used in excess with respect to said starting material.

3. A method in accordance with claim 1 in which said reagent mixture is a combination of (CF$_3$CO)$_2$O and NH$_4$NO$_3$, and said reaction is conducted in nitromethane.

4. A method in accordance with claim 1 in which said reagent mixture is a combination of (CF$_3$CO)$_2$O and HNO$_3$, and said reaction is conducted in nitromethane.

5. A method in accordance with claim 1 in which said reaction is conducted at a temperature of less than about 10° C.

6. A method in accordance with claim 1 in which said reaction is conducted at a temperature of from about 0° C. to about 5° C.

7. A method in accordance with claim 1 in which said acid salt is a hydrohalide salt.

8. A method in accordance with claim 1 in which said acid salt is a member selected from the group consisting of hydrochloride, hydrobromide and hydroiodide salts.

9. A method in accordance with claim 1 in which R is H.HCl.

10. A method in accordance with claim 1 in which R is NO$_2$.

11. A method in accordance with claim 1 in which said starting material and said reagent mixture upon completion of said reaction form a reaction mixture, and said method further comprises crystallizing said compound in crude form from said reaction mixture, followed by recrystallizing said compound from said crude form with ethyl acetate.

12. A method for the preparation of a compound having the formula

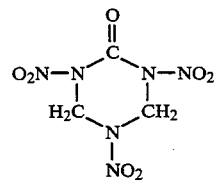

comprising reacting a starting material having the formula

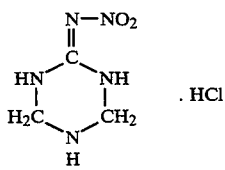

with a reagent mixture comprising a combination of (CF$_3$CO)$_2$O and NH$_4$NO$_3$ in CH$_3$NO$_2$ solvent, said (CF$_3$CO)$_2$O and NH$_4$NO$_3$ each being in excess with respect to said starting material, at a temperature of from about 0° C. to about 5° C., to form said compound.

13. A method for the preparation of a compound having the formula

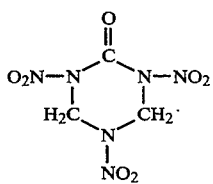

comprising reacting a starting material having the formula

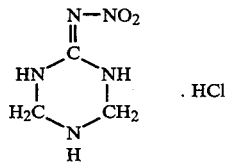

with a reagent mixture comprising a combination of $(CF_3CO)_2O$ and $HNO_3$ in $CH_3NO_2$ solvent, said $(CF_3CO)_2O$ and $HNO_3$ each being in excess with respect to said starting material, at a temperature of from about 0° C. to about 5° C., to form said compound.

14. A method for the preparation of a compound having the formula

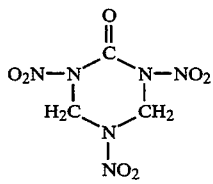

comprising:
(a) reacting a starting material having the formula

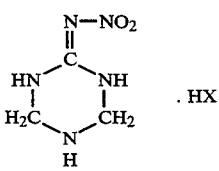

in which X is an anion, with a nitrating agent to form an intermediate having the formula

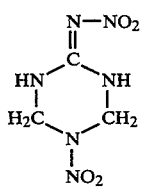

and
(b) reacting said intermediate with a reagent mixture comprising a combination of (1) $(CF_3CO)_2O$ and (2) a member selected from the group consisting of $HNO_3$ and $NH_4NO_3$, to form said compound.

15. A method in accordance with claim 14 in which said nitrating agent is a mixture of concentrated nitric and sulfuric acids.

16. A method in accordance with claim 14 in which X is a member selected from the group consisting of halide, sulfate, phosphate, nitrate and acetate ions.

17. A method in accordance with claim 14 in which X is chloride.

18. A method in accordance with claim 14 in which step (a) is performed at a temperature of from about $-20°$ C. to about $-10°$ C.

19. A method in accordance with claim 14 in which step (b) is begun at a temperature of from about 0° C. to about 5° C.

20. A method for the preparation of a compound having the formula

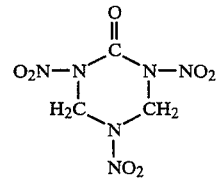

comprising:
(a) reacting a starting material having the formula

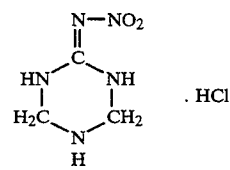

with a mixture of concentrated nitric and sulfuric acids at a temperature of from about $-10°$ C. to about $-20°$ C., to form an intermediate having the formula

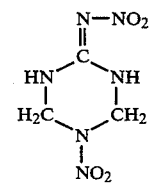

and
(b) reacting said intermediate with a reagent mixture comprising a combination of $(CF_3CO)_2O$ and $NH_4NO_3$, each in excess with respect to said intermediate, in $CH_3NO_2$ solvent at a temperature of from about 0° C. to about 5° C. to form said compound.

21. A method for the preparation of a compound having the formula

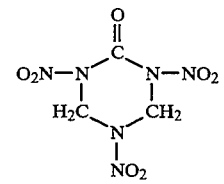

comprising:

(a) reacting a starting material having the formula

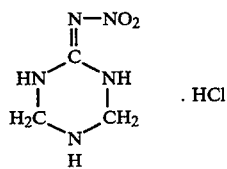

with a mixture of concentrated nitric and sulfuric acids at a temperature of from about −10° C. to about −20° C., to form an intermediate having the formula

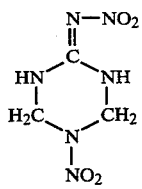

and (b) reacting said intermediate with a reagent mixture comprising a combination of (CF$_3$CO)$_2$O and HNO$_3$, each in excess with respect to said intermediate, in CH$_3$NO$_2$ solvent at a temperature of from about 0° C. to about 5° C. to form said compound.

22. A method for the preparation of a compound having the formula

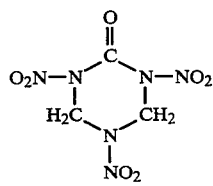

comprising:

(a) reacting hexamethylenetetramine with nitroguanidine in an acidic reaction medium to form a first intermediate having the formula

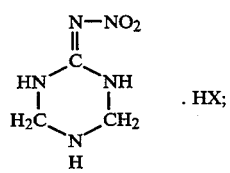

(b) reacting the product of step (a) with a nitrating agent to form a second intermediate having the formula

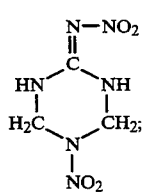

and (c) reacting the product of step (b) with a combination of (CF$_3$CO)$_2$O and NH$_4$NO$_3$ in CH$_3$NO$_2$ solvent to form said compound.

23. A method for the preparation of a compound having the formula

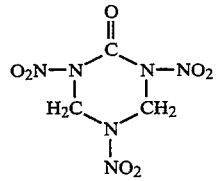

comprising:

(a) reacting hexamethylenetetramine with nitroguanidine in an acidic reaction medium to form a first intermediate having the formula

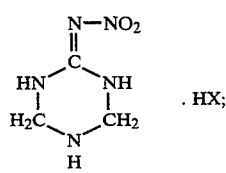

(b) reacting the product of step (a) with a nitrating agent to form a second intermediate having the formula

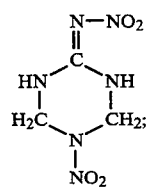

and (c) reacting the product of step (b) with a combination of (CF$_3$CO)$_2$O and HNO$_3$ in CH$_3$NO$_2$ solvent to form said compound.

24. A method in accordance with claims 22 or 23 in which said acidic reaction medium of step (a) is concentrated aqueous HCl.

25. A method in accordance with claims 22 or 23 in which step (a) is conducted at a temperature of from about 20° C. to about 50° C.

26. A method in accordance with claims 22 or 23 in which said nitrating agent of step (b) is a mixture of concentrated nitric and sulfuric acids.

27. A method for the preparation of a compound having the formula

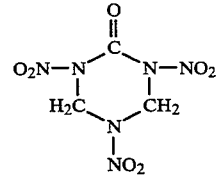

comprising:

(a) reacting hexamethylenetetramine with nitroguanidine in concentrated aqueous HCl at a temperature of from about 20° C. to about 50° C. to form a first intermediate having the formula

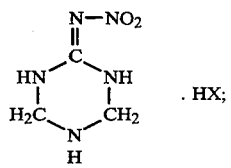

(b) reacting the product of step (a) with a mixture of concentrated nitric and sulfuric acids at a temperature of from about −20° C. to about −10° C., to form a second intermediate having the formula

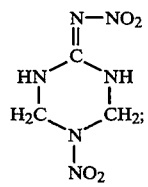

and (c) reacting the product of step (b) with a reagent mixture comprising a combination of (CF$_3$CO)$_2$O and NH$_4$NO$_3$, each in excess with respect to said intermediate, in CH$_3$NO$_2$ solvent at a temperature of from about 0° C. to about 5° C. to form said compound.

28. A method for the preparation of a compound having the formula

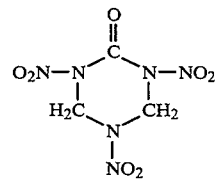

comprising:

(a) reacting hexamethylenetetramine with nitroguanidine in concentrated aqueous HCl at a temperature of from about 20° C. to about 50° C. to form a first intermediate having the formula

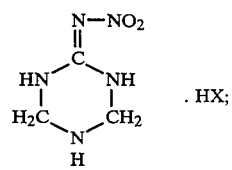

(b) reacting the product of step (a) with a mixture of concentrated nitric and sulfuric acids at a temperature of from about −20° C. to about −10° C., to form a second intermediate having the formula

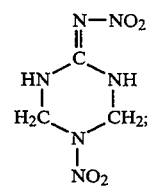

and (c) reacting the product of step (b) with a reagent mixture comprising a combination of (CF$_3$CO)$_2$O and HNO$_3$, each in excess with respect to said intermediate, in CH$_3$NO$_2$ solvent at a temperature of from about 0° C. to about 5° C. to form said compound.

* * * * *